(12) United States Patent
Datla et al.

(10) Patent No.: US 8,753,856 B2
(45) Date of Patent: Jun. 17, 2014

US008753856B2

(54) STABLE BIOCATALYSTS OF PENICILLIN ACYLASE AS GEL AGGREGATES AND THE PROCESS OF MANUFACTURE THEREOF

(75) Inventors: Anupama Datla, Maharashtra (IN); Rajasekar Vyasarayani Williams, Maharashtra (IN); Trupti Krishnakant Ashar, Maharashtra (IN); Pavel Kyslik, Praha (CZ); Stanislav Becka, Praha (CZ)

(73) Assignee: Fermenta Biotech Ltd., Thane (West) Maharashtra, IN (US)

( * ) Notice: Subject to any disclaimer, the term of this patent is extended or adjusted under 35 U.S.C. 154(b) by 109 days.

(21) Appl. No.: 12/989,716

(22) PCT Filed: Nov. 14, 2008

(86) PCT No.: PCT/IN2008/000769
§ 371 (c)(1),
(2), (4) Date: Oct. 26, 2010

(87) PCT Pub. No.: WO2010/055527
PCT Pub. Date: May 20, 2010

(65) Prior Publication Data
US 2011/0287509 A1    Nov. 24, 2011

(51) Int. Cl.
*C12N 11/04* (2006.01)
*C12N 11/08* (2006.01)
*C12N 11/02* (2006.01)
*C12N 11/14* (2006.01)
*C12P 1/04* (2006.01)
*C12N 1/20* (2006.01)

(52) U.S. Cl.
USPC ........... 435/182; 435/180; 435/177; 435/176; 435/170; 435/252.33

(58) Field of Classification Search
None
See application file for complete search history.

(56) References Cited

U.S. PATENT DOCUMENTS

| 4,727,030 | A | 2/1988 | Ishimura et al. |
| 4,978,619 | A | 12/1990 | Kajiwara et al. |
| 5,093,253 | A | 3/1992 | Nolan |
| 5,846,762 | A | 12/1998 | Woodward |
| 6,060,268 | A | 5/2000 | De Vroom |
| 2006/0234366 | A1* | 10/2006 | Smith et al. ................ 435/189 |

FOREIGN PATENT DOCUMENTS

EP    1088887    9/1999

OTHER PUBLICATIONS

Becka, S; Skrob, F; Plhackova, K; Kujan, P; Holer, P; Kyslik, P "Cross-linked Cell Aggregates of Trigonopsis variabilis: D-Amino Acid Oxidase Catalyst for Oxidation of Cephalosporin C" Biotechnol. Lett, Feb. 2003, 25(3), pp. 227-233.*
Sheldon, R.A, 2007, "Immobilization of enzymes as cross—linked enzyme aggregates: a simple method for improving performance," Biocatalysis in the Pharmaceutical and Biotechnology Industries, 351-362.
Cheng, S, 2006, "Immobilization of permeabilized whole cell penicillin G acylase from *Alcaligenes faecalis* using pore matrix crosslinked with glutaraldehyde," Biotechnology Letters, vol. 28, 1129-1133.
Cao, L, 2001, "Cross-linked aggregates of penicillin acylase: robust catalysts for the synthesis of β-lactam antibiotics," Journal of Molecular Catalysis: Enzymatic I†: 655-670.
Cao, L, 2000, "Cross-Linked enzyme aggregates: A Simple and Effective Method for the Immobilization of Penicillin Acylase," Organic Letters, vol. 2, No. 10:1361-1364.
Wilson, L, 2004, "Encapsulation of Crosslinked Penicillin G Acylase Aggregates in Lentikats: Evaluation of a Novel Biocatalyst in Organic Media," Willey Periodicals, Inc.: 558-562.
Hassan, C, 2000, "Structure and Applications of Poly(vinyi alcohol) Hydrogels Produced by Conventional Crosslinking or by Freezing/Thawing Methods," Advances in Polymer Science, vol. 153:37-40.
Gelatin manufactures institute of America-"Geletin information, news, history and more.", GMIA, Jul. 14, 2009, 7 pages.
PCT International Search Report for Fermenta Biotech Limited, International App'l No. PCT/IN2008/000769, filed Nov. 14, 2008, Dated Aug. 20, 2009, 3 pages.
PCT International Written Opinion for Fermenta Biotech Limited, International App'l No. PCT/IN2008/000769, filed Nov. 14, 2008, Dated Aug. 20, 2009, 3 pages.
Wilson, L, 2004, "Co-Aggregation of Penicillin G Acylase and Polyionic Polymers: An Easy Methodology to Prepare Enzyme Biocatalysts Stable in Organic Media," Biomacromolecules, vol. 5, No. 3:852-857.
Cao, L, 2005, "Immobilised enzymed: science or art?"Current Opinion in Chemical Biology vol. 9:217-226.
Maresova, et al., "A Chemostat Culture as a Tool for the Impreovement of a Recombinant *E.coli* Strain Over-Producing Penicillin G Acylase", Biotechnology and Bioengineering, vol. 75, No. 1, Oct. 5, 2011, pp. 46-52.

* cited by examiner

*Primary Examiner* — Chris R Tate
*Assistant Examiner* — Aaron J Kosar
(74) *Attorney, Agent, or Firm* — Kramer Amado, P.C.

(57) ABSTRACT

The present invention provides a stable and viable biocatalyst with high activity and operational stability and method of immobilization thereof. The immobilization process is based on the principle of entrapment of partially purified enzyme precipitate which is simultaneously aggregated by cross linking agent like glutaraldehyde and further entrapped in a combination of natural polymer like gelatin and synthetic polymer like polyvinyl alcohol with effective gelation under mild conditions of temperature and pH, resulting in a stable biocatalyst. The enzymes immobilized by the above process include Penicillin acylase from r*E. coli* RE III (pKA18), Novel Penicillin acylase from *Achromobacter* sp (CCM4834) expressed in r*E. coli* BL21 (pK1P1) CCM 7394 and r*E. coli* RE III (pKX1P1).

17 Claims, 4 Drawing Sheets

Figure 1:
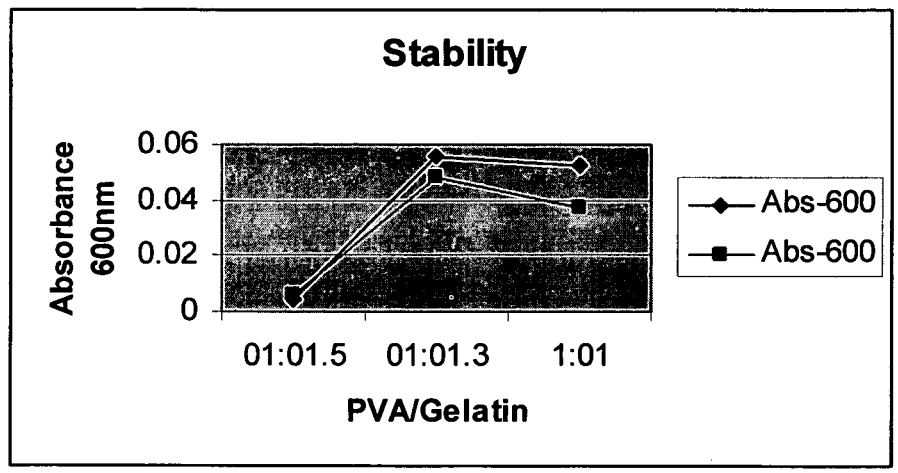

STABLE BIOCATALYSTS OF PENICILLIN ACYLASE AS GEL AGGREGATES AND THE PROCESS OF MANUFACTURE THEREOF

This application is the National Stage of International Application PCT/IN2008/000769, filed Nov. 14, 2008, which is hereby incorporated in its entirety by reference into this application.

TECHNICAL FIELD

The present invention relates to a stable and viable biocatalyst with high activity and operational stability. The invention further relates to process of preparation of biocatalyst using a method of simple immobilization combined with simultaneous precipitation, cross linking and entrapment, which is easy to scale-up, involves the use of non toxic materials for immobilization.

BACKGROUND AND PRIOR ART

The enzymes, if soluble in water or in a mixture of water and other co-solvent, can be used for a single conversion cycle. To overcome this drawback, the technique of immobilization has been developed.

The increasing use of enzymes as catalysts in industrial processes has led to increasing demand of enzymes in immobilized form. The immobilized enzymes frequently termed as 'biocatalysts' are widely used for industrial organic synthesis and biotransformation. According to a 2002 review, there are more than 130 biotransformation currently performed in an industrial scale using biocatalyst, mostly in the manufacture of pharmaceutical intermediates and other fine chemicals. Over the years this widely accepted technique of immobilization, has witnessed significant changes and improvement. Today the immobilizations are directed to specific use and tailor made for purpose of use like immobilized antibodies, macromolecular complexes and structural proteins. Immobilized enzymes (biocatalyst) however command greater attention.

The biocatalysts can be produced using whole living or dead cells or the enzymes made thereof. The source of enzyme may vary from plants and animals to microorganisms. The expanded pool of enzymes and advances in protein engineering has made it possible to produce economically viable biocatalyst on a commercial scale.

The enzymatic reactions are highly specific which is based on specific properties of the enzymes such as substrate specificity, activity, enantio-selectivity, productivity, stability, pH and temperature optimum profiles and so forth. The commercialization of many enzymes is hampered by lack of operational stability coupled with relatively high price. This impediment can be overcome if one can find an effective method for immobilization. If successful, this not only results in improved selective properties, operational stability but allows for the facile separation, reuse of enzyme and simplifies down stream processing. Hence to develop a suitable biocatalyst the selection of suitable immobilization process becomes crucial.

Conceptually, immobilizations have several approaches. Amongst them are adsorption, carrier binding, entrapment, and cross linking. Physical adsorption relies on the affinity of enzyme with the support. Though simple, the interaction is weak and the enzyme can be readily desorbed and lost. Carrier binding involves connecting the enzyme to a water insoluble support by ionic or covalent bonds. This process has a disadvantage of partial inactivation of the enzyme molecule because of strong chemical bond. Also the target enzymes are required to be in more purified form which eventually increases the cost of catalyst production.

The third method of immobilization involves entrapment of a given enzyme in gel or microcapsules made of suitable organic or inorganic natural or synthetic polymers. This method has an advantage as it does not entail protein inactivation due to strong covalent bond modification. The formation of pores of a given size of the selected gel matrix or fibers can be suitably adjusted so as to hold up high molecular weight enzyme molecules. And yet permit selective passage of small reactant molecules and consequently, preclude the otherwise possible separation of the enzyme from the carrier. More often the entrapment method is combined with cross linking method in a number of configurations. Specific bi-functional agents like glutaraldehyde which form covalent bonds with the protein molecule resulting in formation of large aggregates. Cross linking also imparts rigidity and physical strength to the entrapped enzyme. In addition, supports generally used in entrapment seem to be compatible with whole cells and enzymes with low specificity and lower purity as compared to those used in covalent binding. This essentially makes the process more cost effective.

Ample Literature is available on use of different materials and products of immobilized enzymes formed thereof.

An article on "Immobilization of permeabilized whole cell penicillin G acylase from *Alcaligenes faecalis* using pore matrix cross linked with glutaraldehyde" by Cheng, Shiwei et al, (Biotechnology Letters, Volume 28, Number 14, July 2006, pages 1129-1133) discloses the activity of penicillin G acylase from *Alcaligenes faecalis* increased 7.5-fold when cells were permeabilized with 0.3% (w/v) CTAB. The treated cells were entrapped by polyvinyl alcohol crosslinked with boric acid, and crosslinked with 2% (v/v) glutaraldehyde to increase the stability. The conversion yield of penicillin G to 6-aminopenicillanic acid is 75% by immobilized system in batch reaction. No activity is lost after 15 cycles and about 65% enzyme activity is retained at the end of the $31^{st}$ cycle.

U.S. Pat. No. 4,727,030 and U.S. Pat. No. 4,978,619 also reports use of gel matrix for immobilization of enzymes or cells.

Recently, Cross linked Enzyme Aggregates (CLEAs) as immobilized enzymes, has gained much importance and is looked upon as lucrative alternative to use of polymers for immobilization. However, its industrial viability needs to be further evaluated as the CLEA particles of most of the enzyme is too small and poses serious filtration problems. Though, CLEA offers high advantage of very high specific activity of enzyme, this operational issue of filtration impediments commercial exploitation.

Significant work has been reported and published in this particular field but few techniques have been successful at commercial level. Penicillin acylases of microbial origin are currently used in immobilized form for the synthesis of intermediates of beta lactam antibiotics. Literature reports whole cell penicillin acylase catalyst, enzyme immobilized by entrapment or covalently linked purified enzyme forms, including catalysts based on Cross Linked Enzyme Crystals (CLEC) and Cross Linked Enzyme Aggregates CLEA.

Penicillin acylase immobilized on cross linked p-xylene diamine with glutaraldehyde (Poly-XDA-GA-PA), assemblase(r) 7500 entrapped in Gelatin and Chitosan, PGA-450 FERMASE PA 250, whole cell cross linking on Polyethyleneimine supports, are to name a few.

U.S. Pat. No. 5,846,762 claims use of gelatin with propylene glycol & alginate with glutaraldehyde to form gel beads containing entrapped enzyme of different enzymes.

In U.S. Pat. No. 6,060,268 claims preparation of an immobilized penicillin G acylase by covalent bonding to a crosslinked gelled gelatin and other polymers such as alginate chitosan or polyethylene imine.

By whichever method immobilized enzyme is prepared, an ideal industrial immobilized enzyme has to meet several criteria, such as recyclability, broad applicability, cost effectiveness, environmental and safety issues. Further, the conditions on an industrial scale are more severe for immobilizations as there are problems of inactivation of cells or enzymes due to polyfunctional reagents used. Also the low physical strength of immobilized biomaterial may clog the pores leading to diffusional limitations and hence limiting long time catalyst usage. Consequently, the disposal of deactivated immobilized enzymes also has to be accounted for an industrial scale. This is especially evident in case of certain enzymes like immobilized penicillin acylase which are used in tons for production of semisynthetic beta-lactam antibiotics, both in the preparation of intermediates as well as in final drug molecules.

Therefore, there is a need in the art to develop a biocatalyst having high activity and operational stability with multiple usage in hydrolytic and synthetic biocatalyses namely in the area of biotransformation of semisynthetic beta-lactam antibiotics, which the present inventors have achieved in this invention.

SUMMARY OF THE INVENTION

In accordance with the above, the present invention provides a stable and viable biocatalyst with high activity and operational stability and method of immobilization thereof. The immobilization process is based on the principle of entrapment of partially purified enzyme precipitate which is simultaneously aggregated by cross linking agent like glutaraldehyde and further entrapped in a combination of natural polymer like gelatin and synthetic polymer like polyvinyl alcohol with effective gelation under mild conditions of temperature and pH, resulting in a stable biocatalyst.

Thus the stable biocatalyst obtained is an efficient immobilized product, in which enzyme is retained in the gel matrix and is not diffusing out of it. The gel material forms a stable matrix which can not only resist mechanical stress and prevent leakage of the enzyme, but also help better mass transfer of the enzyme reactants, thus lowering the barrier of concentration gradients.

In one aspect, the present invention uses penicillin acylase enzyme from rE. coli RE III (pKA18) which shows high hydrolytic activity and Novel Penicillin Acylase enzymes from rE. coli BL21 CCM7394 (pKX1P1) and rE. coli REX III (pKX1P1) which show high synthetic activity to prepare immobilized, stable and viable biocatalyst with high activity and operational stability.

In an alternative aspect, whole cells are also used. Other enzymes like lipase, protease, aldolases, isomerases can also be immobilized by similar process.

In another aspect, partially purified enzyme is used after effective precipitation at low temperatures with ammonium sulphate, the concentration of which is optimized for each of the enzymes used and is in the range of 20-50 gram/gram of protein. Further, enzyme in precipitate form is crosslinked with bifunctional agent like glutaraldehyde (GA) to form stable aggregates. This particular stage includes nonspecific proteins which probably aid in the cross linking stage and increases the size of the aggregates formed, which in turn can be retained in entrapment and prevent diffusion.

Abbreviations:
6-APA: 6-aminopenicillanic acid
7-ADCA: 7-deacetoxy cephalosporanic acid
PAA: phenylacetic acid
rE. coli: recombinant Escherichia coli
w/w: weight by weight
w/v: weight by volume
v/v: volume by volume
w: weight
HPGMe: D-p-hydroxyphenyl glycine methyl ester hydrochloride
PVA: polyvinyl alcohol
GA: glutaraldehyde
U: activity units Activity is defined as the amount of enzyme catalyzing the formation of 1 micromole of substrate utilized or 1 micromole of product formed in unit time under standard defined conditions for each enzyme.

DETAILED DESCRIPTION OF FIGURES

FIG. 1 indicates the stability of immobilized biocatalyst (Blue line: Example 1 i.e enzyme precipitate obtained rE. coli REIII (pKA18), Pink line: Example 2 i.e. enzyme precipitate obtained from rE. coli BL21 CCM7394).

Figure 2:
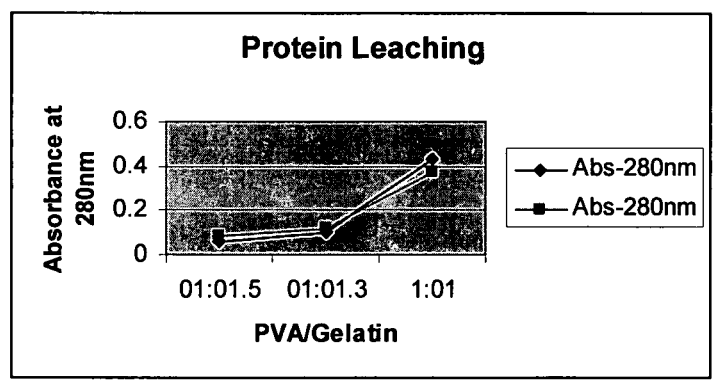

FIG. 2 indicates the extent of protein leach (Blue line: Example 1 i.e enzyme precipitate obtained rE. coli REIII (pKA18), Pink line: Example 2 i.e. enzyme precipitate obtained from rE. coli BL21 CCM7394).

Figure 3:
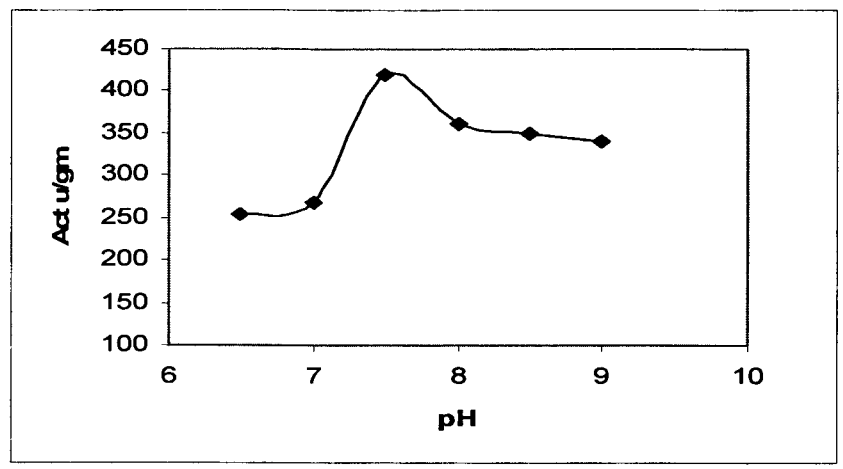

FIG. 3 indicates the profile of Penicillin G hydrolytic activity of biocatalyst

Figure 4:
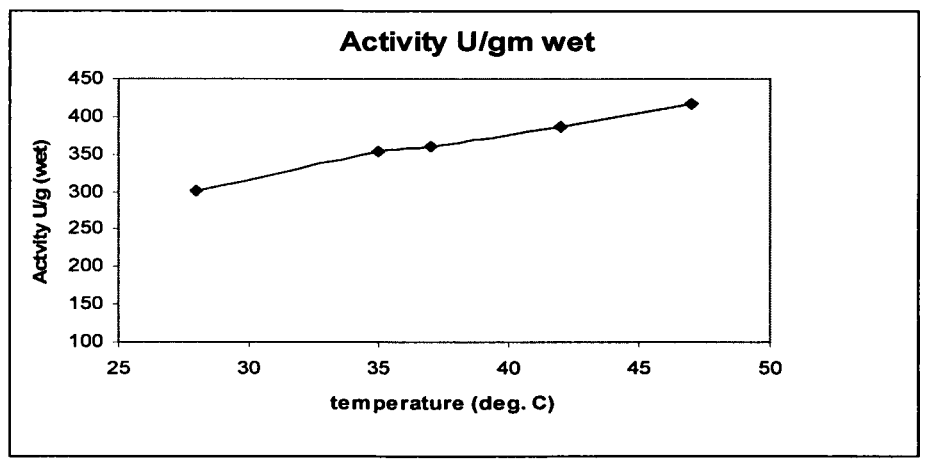
Figure 5:
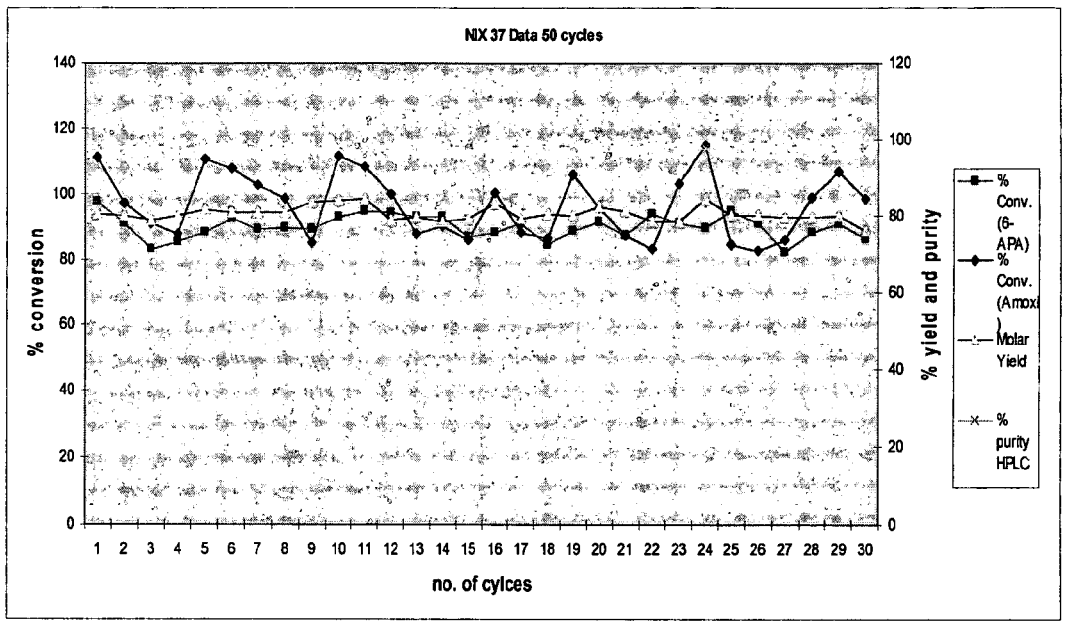
Figure 6:
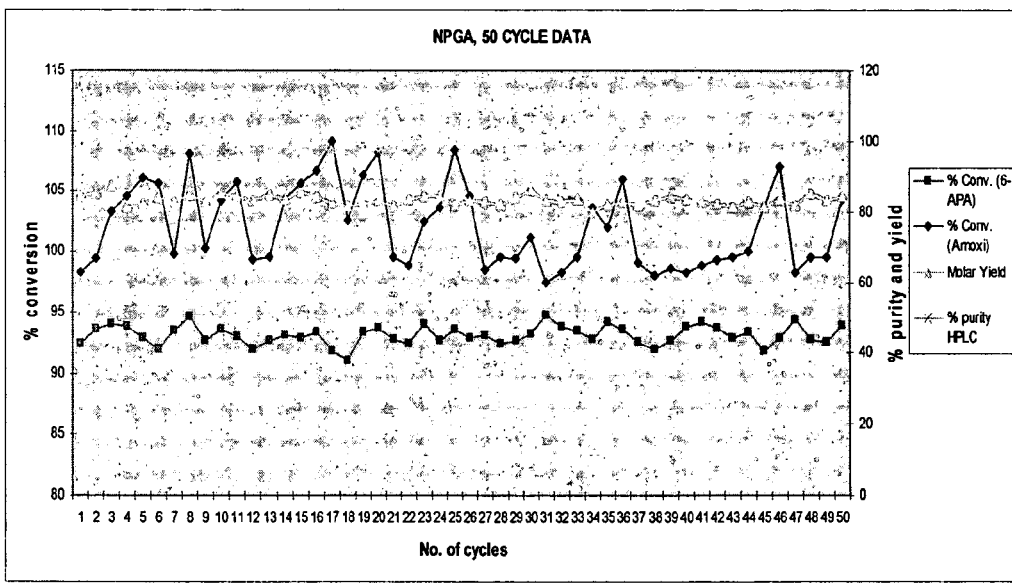
Figure 7:
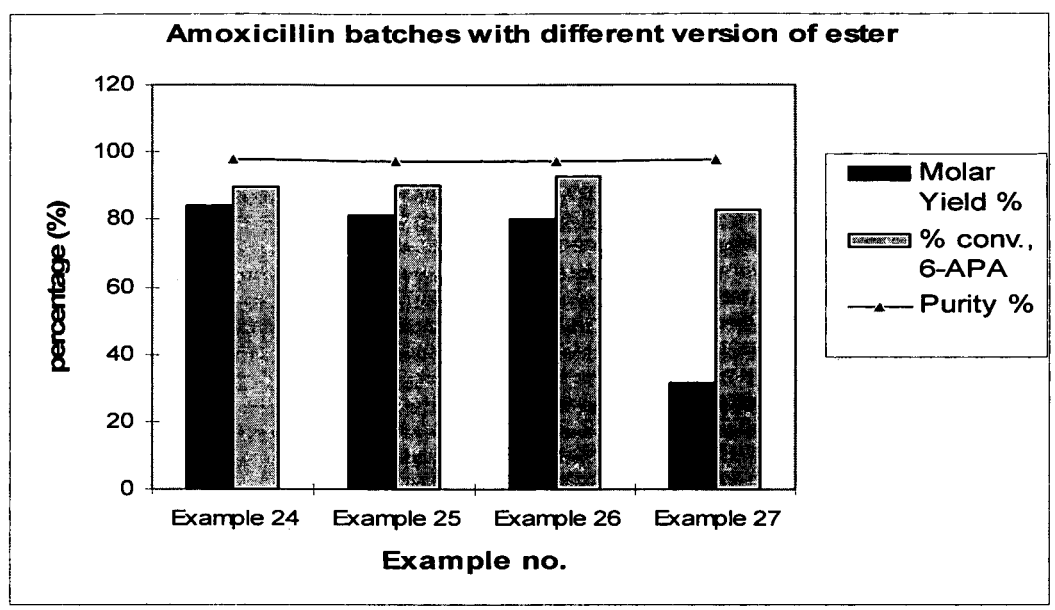

FIG. 4 indicates the effect of reaction temperature on the hydrolysis of Penicillin G activity with biocatalyst FIG. 5 indicates the enzymatic synthesis of Amoxicillin used for 30 repeated conversion cycles FIG. 6 indicates the enzymatic synthesis of Amoxicillin used for 50 repeated conversion cycles FIG. 7 indicates the Amoxicillin batches with different version of ester

DETAILED DESCRIPTION

The invention will now be described in detail in connection with certain preferred and optional embodiments, so that various aspects thereof may be more fully understood and appreciated.

Accordingly, the present invention comprises use of enzyme as precipitated aggregates obtained by salting out crude protein solution at low temperatures to form partially soluble precipitate and further cross linking with aid of cross linking agent to form aggregates.

In a preferred embodiment, the present invention provides a stable and viable biocatalyst with high activity and operational stability prepared by a process comprising the following steps:
  (a) precipitating simultaneously and cross linking of enzyme solution with ammonium sulphate and glutaraldehyde at temperature between 1° C. to 2° C. to obtain Cross Linked Enzyme Aggregates;
  (b) Variation of enzyme linking with ammonium sulphate and glutaraldehyde at higher temperature between 18 to 23 deg C., more specifically between 20-21 deg C. to obtain self immobilized Cross linked enzyme aggregate;
  (c) entrapping the said aggregated enzyme in a solutions of 10% w/w polyvinyl alcohol and 10% w/w gelatin at low temperature;

(d) gelation is further allowed to occur with cold incubation at 5° C. for 12 hours;

(e) obtaining gel enzyme by sieving through 150 micron to obtain uniformly distributed gel aggregates and (f) re-crosslinking further gel aggregates with glutaraldehyde at 30° C., at pH 7.5-7.6 for 30 minutes to improve the structural stability.

In preferred embodiment, the said enzyme is selected from penicillin acylase enzyme obtained from r*E. coli* RE III (pKA18) which shows high hydrolytic activity and Novel Penicillin Acylase enzymes obtained from r*E. coli* BL21 CCM7394 (pKX1P1) and r*E. coli* REX III (pKX1P1).

Principally, precipitating agents used are inorganic salts or biopolymers or solvents or combinations of these. The selectivity is based on enzyme being precipitated and precipitant not having a negative effect on enzyme activity and stability. Some well known and conventionally used precipitants include quarternary ammonium salts and polyethylene glycol and solvents such as methanol, ethanol, isopropyl alcohol, butanol, acetone and tert butyl alcohol. Polyamines can be used but these are known to react with cross linking process hence ammonium sulphate is used, preferably.

The amount of ammonium sulphate is generally used up to its water saturation concentration. Reported literature states that the percentage varies between 10-80%. However, it has to be optimized for specific enzyme and process involved. Therefore, in the present embodiment, the concentration of ammonium sulphate used is based on protein concentration of the enzyme solution. The optimized concentration used is preferably between 20-30 gram per gram of proteins. So the saturation concentration range varies between 50-70%. Precipitation is preferably performed at low temperatures between 0-5° C. preferably between 1 to 2° C. to obtain gel aggregates.

The pH is maintained between 7 to 7.5 for period of time ranging from 30 minutes to 60 minutes and precipitate is allowed to stand at 5° C. for 12 hrs for better aggregation. The precipitated form is separated by centrifugation. The number of enzyme molecules and way they are folded in the aggregate may have a profound effect on the activity of the enzyme. During aggregation, the solubility of the enzyme decreases. During this stage, the enzyme might denature so the time of aggregation and temperature are critical and optimized for the process.

Cross linking is carried out in buffer for 5 minutes and at 1-2° C. with fast addition of cross linking agent. The buffer used is 0.1M of sodium phosphate buffer with pH range between 6.5-7.5, for optimizing the enzyme.

As a variation to the above process, the cross linking time, temperature and addition of glutaraldehyde was altered in one of the embodiment to form an insoluble precipitate as cross linked enzyme aggregate (CLEA)

Although various cross linking agents are known, glutaraldehyde remains a cheap and most versatile agent. The range of concentrations has been studied for each of the enzymes. In case of Penicillin acylase, the best results are obtained with concentration of 1.7%-2.0%. However the preferred concentration is between 1.7-1.8% calculated with respect to final weight of the product. Similarly for novel penicillin acylase, the concentration preferred is in the range of 1.0-1.5%.

In the preferred embodiment of the invention, various carrier materials are used for the process of entrapment. Both organic and inorganic, occurring naturally or synthesized, acrylamide, chitosan, sodium alginate, polyvinyl alcohol, gelatin are used. A combination of two or more materials in suitable concentrations has resulted in formation of stable immobilized biocatalyst. The best suited carriers are further optimized for the product development.

Normally, the types of materials used for entrapment varies with each process and enzyme. The materials most commonly preferred are synthetic like acrylamide or natural like calcium alginate, karrageennan, gelatin etc. The choice varies depending on factors influencing the process. Though monomers like acrylamide form relatively non reactive polymer, the product may contain traces of unpolymerized monomer which is potentially hazardous to the handler and further have disposal problems. Also the polymerization initiator Dimethylaminopropionitrile is highly toxic and must be handled with great care.

Entrapment in calcium alginate gels allows immobilizations under mild conditions and is widely used for whole cell immobilizations. However, it has lesser probability of scale up as these systems has inherent problem of operational stability and enzyme leaching effect.

In addition to use of acrylamide, chitosan, calcium alginate; gelatin also shows good potential gelling properties. Gelatin is an animal protein and tends to gel in solution at particular temperature. Based on the viscosity and gel strength of gelatin used, the gel can be strengthened by mixing with other polymeric materials. The pore size of such gel can be controlled by optimizing the concentration of gelatin and other polymer used.

Further, the aqueous mixture of PVA with enzyme at lower temperature forms a dehydrated gel which is molded into desired shape. However, addition of any other polymeric material may further assist in water retention and increase in mechanical strength but requires optimization.

Since acrylamide has been conventionally known to be used as polymerizing agent, it is used additionally with (PVA) and gelatin; however the product yields are less as compared to that obtained without use of acrylamide with gelatin and polyvinylalcohol. One of the reasons being there was poor polymerization which is evident from the formation of very soft material. This possibly led to enzyme leaching from the immobilized enzyme, thus low yields. Though, it is possible to improve the crosslinking and polymerization, the choice was always to avoid using a hazardous material like Acryl amide. Hence, further work was not continued.

When chitosan is used instead of PVA, the final product has lower stability. Chitosan has been reported to be used in mixture with gelatin for immobilization (Assemblase), however the concentration of gelatin and chitosan needs to be optimized further to improve the final product.

In view of the above disadvantages, the present inventor have used polyvinyl alcohol as polymer along with gelatin, which gives better entrapment polymer as compared to combination with acrylamide, or calcium alginate, chitosan for immobilization of penicillin acylase.

In the present invention, the Polyvinyl alcohol used is with molecular weight is 125000 having viscosity 35-50 cs. The Gelatin used is of the pharmaceutical grade. It is preferable to use PVA with high molecular weight more than 100000.

PVA which are commercially available have fairly wide molecular distribution, the polydisperity indices range from 2 to 5. Molecular weight affects many properties such as adhesion, crystallizability, mechanical strength and diffusivity.

The molecular weight of PVA is directly proportional to the degree of polymerization. The degree of polymerization affects the solubility of PVA in water. PVA with high degree of polymerization and hydrolysis has molecular weight more than 77000, wherein the hydrophobic acetate groups weaken the intra molecular hydrogen bonding of adjoining hydroxyl groups. Hence the temperature is raised well above 70° C. for dissolution to occur. It has to be further cooled before addition to the enzyme.

PVA used for pharmaceutical purpose can be crosslinked with agents such as Glutaraldehyde which tend to be insoluble in water. PVA has a tendency to form Hydrogels which can be described as hydrophilic, cross linked polymer. This particular property of PVA is particularly useful in immobilization as it tends to retain water which in turn prevents dehydration of enzyme and helps retain its active form. PVA by virtue of its macromolecular form is capable of forming a gel with cross linking agent and hence suitably used in the present embodiment.

Another polymer, Gelatin, is widely used in food and pharma industry. Gelatin has natural tackiness which assists in agglomeration of particles. Gelatin solutions are used as the binder in this process to form larger agglomerates containing the active, binder, diluents and glidants. The use of gelatin in the granulation process provides an efficient means for reducing fines and maintaining physiological inertness. In suspension polymerization, gelatin functions to control particle size as well as to prevent coalescence of the particles Gelatin is used in solution form, the concentration of which varied between 10 to 20%, Hot water is used to dissolve gelatin and stirred to form a clear solution before addition to the enzyme for immobilization. Both PVA and Gelatin concentrations act as prepolymers suitable for gelation and have been optimized in the present process based on the desired product properties. The polyvinyl alcohol concentration is between 4.5-7.5% of the weight of the final product, whereas the gelatin concentration is between 1-5%, more precisely between 1.2-1.5 times of the weight of the polyvinyl alcohol used.

Further, entrapment within polymers is aided by cross linking with bifunctional agents like glutaraldehyde (GA). The use of GA as cross linker has been widely reported. By optimizing the concentration of GA to be used for particular enzyme so as to retain its catalytic activity, it is possible to obtain a relatively stable product. GA forms Schiff's base with amino groups on protein molecules and hence helps better cross linking, an irreversible linkage is obtained with reduction of Schiff's bases with sodium borohydride, which is not found suitable for penicillin acylase as it results in loss of enzyme stability.

In present process, gelatin being protein; the presence of gelatin further enhances the linkages of GA resulting in better entrapment and stable product.

The product and the process described in the present invention are particularly advantageous because the materials are readily available, are non toxic, may pose lesser disposal problems, have probability of commercialization, and the use of process can be extended for other enzymes.

The efficiency of immobilized penicillin acylase or novel penicillin acylase is determined by comparing their parameters with native enzyme. The enzyme activity in terms of hydrolysis and synthesis are higher than that of native form. The yields in terms of weight and activity are acceptable with industrial levels.

The present invention further encompasses preparing solutions of entrapment agents, polyvinyl alcohol and Gelatin. A 10% w/w solution of each agent is prepared in warm water and heated at 90° C. to achieve dissolution. Each of the above prepared solution is added to the aggregated enzyme solution at 5° C. and stirred at 200 rpm with overhead stirrer enabled with teflon blade to form a gel. The ratio of PVA and Gelatin in the mixture studied with respect to Penicillin acylase immobilization is in the range of 1:1.1 to 1:1.5, most preferably 1:1.3. The gel is further allowed to stand at 5° C. for 12 hours for gelation to occur. During this time, the unreacted glutaraldehyde probably reacts with gelatin which seems to harden the gel further and improve the structure of the product. The gelated form is then sieved mechanically in #30 mesh to obtain spherical gel beads of suitable size. Amongst all the shapes, spherical beads are most preferred, as these provide the highest surface/volume ratio and the present method allows the flexibility of obtaining the same. These beads are further recrosslinked with 0.5%-0.75% glutaraldehyde at 30° C. for 40 minutes at pH ranging between 7.2-7.5. The further cross linking improves the stability of the product and prevents any leaching of the enzyme and support materials and hence represents a very critical step in the process. The leaching of support materials or protein are checked by determining the absorbance of ishings 280 nm and 600 nm. The gel beads were washed with water to remove traces of unreacted reagents and monomers. Further washing is done with water and immobilized product is stored in 50 mM sodium phosphate buffer containing 500 ppm of ethyl paraben. The final product referred to as immobilized biocatalyst had dry weight in the range of 15-20% with 98% of particles having size between 100-300 microns.

In another embodiment biocatalyst is prepared using combination of other encapsulating materials. A 15% solution of acrylamide, N,N-methylenebisacrylamide and gelatin. The solution contained each component in the ration of 19:1:10 respectively.

In acrylamide based immobilizations, the completion of polymerization is ensured by addition of accelerating agents of which TEMED and 1,2, dimethylaminopropionitrile are more commonly used.

In another embodiment, Temed is replaced with 1,2,dimethylaminopropionitrile, where the biocatalyst obtained is different in terms of yield and further use is restricted due to reasons of toxicity of the material.

In another embodiment, PVA or chitosan is used instead of Gelatin in combination with acrylamide and N,N-methylenebisacrylamide.

The biocatalyst prepared is studied for their reusability in terms of 6-APA, synthesis.

Dry weight of biocatalyst is determined gravimetrically in moisture analyzer (Sartorius) using 0.3-0.5 gm of sample spread in pre-dried aluminium plate and heated at 105° C. for 30 minutes.

Further, the Penicillin G hydrolysis activity is determined using the biocatalyst obtained in the present invention by alkali metric titration using 25 mM Penicillin G, 50 mM sodium phosphate buffer pH 8.0, at 37° C.

Similarly, the Cephalosporin G hydrolysis activity is determined by alkali metric titration using 25 mM Cephalosporin G solution prepared in 50 mM sodium phosphate buffer pH 8.0, at 37° C.

Further, amoxicillin synthetic activity is determined using 44 mM 6-APA and 66 mM HPGMe, at pH 6.3 and 40° C. The reaction is carried out for 30 mins, followed by HPLC analysis, wherein HPLC analysis is done with Inertsil C8 column, mobile phase 1.2 ml/min flow rate with peak determined at 215 nm The enzymes used for immobilization to form the biocatalyst product are penicillin acylase and novel penicillin acylase. These are obtained by extraction of enzyme from biomass of recombinant $E.\ coli$ as mentioned above.

The weight of final product is between 1.4-2.0 times the weight of respective enzyme added and the dry weight is between 15-20%.

The yield of biocatalysts generated by immobilization of penicillin acylase from recombinant *E. coli* REXIII (pKA18) is between 45-65% with respect to activity loaded in the process.

In another preferred embodiment, the performance of biocatalyst is evaluated by reusing the immobilized biocatalyst in repeated conversion cycles for hydrolysis of penicillin G to 6-APA. The hydrolysis of Penicillin G is carried out at 250 ml reactor vessel equipped with baffled stirrer, pH and temperature sensor with 8% penicillin G concentration at 28 degrees and using 1:1 w/w of wet biocatalyst and Penicillin G potassium salt. The pH is maintained by addition of 2M ammonia solution. The reaction is terminated based on reduced consumption of ammonia solution up to less than 100 µl. The reaction volume is removed by filtration and replaced by fresh penicillin solution for the next cycle with same biocatalyst. 6-APA formed is determined by HPLC using Zorbax SB C18 column, mobile phase 0.05M KH2PO4 (pH 7.0):acetonitrile in ratio 70:30, flow rate 1 ml/min and peak is determined at 215 nm which shows almost no loss in activity for at least 50 cycles.

Similarly in another embodiment, the biocatalyst prepared is also studied similarly with respect to Cephalosporin G hydrolysis using 4.5% Cephalosporin G. The biocatalyst is reused in 50 repeated conversion cycles for the hydrolysis. The reaction time is 45-50 minutes, Te conversion of Cephalosporin G to 7-ADCA 86% to 87% on molar basis and 97-98% purity. The analytical determination is similar to that used for Penicillin G as mentioned above.

The novel penicillin acylase obtained from r*E. coli* BL21 CCM 7394 (pKX1PI) and r*E. coli* REIII (pKXIPI) (DVK strain) are also immobilized similarly. The yield of biocatalyst in terms of synthetic activity for amoxicillin is between 40-65% with respect to activity loaded in the process. The organisms r*E. coli* BL21 CCM 7394 pKX1PI) and r*E. coli* REIII pKXIPI) (DVK strain) have been deposited under the Budapest Treaty with the following International Depository Authority:

Czech Collection of Microorganisms CCM
Masaryk University
Faculty of Science
Tvrdého 14
602 00 Brno
Czech Republic The organism r*E. coli* BL21 CCM 7394 (pKX1PI) was deposited on Dec. 4, 2006, and assigned the accession number CCM 7394. The organism r*E. coli* REIII (pKXIPI) (DVK strain) was deposited on Dec. 20, 2010, and assigned the accession number CCM 7883.

Each of the biocatalyst is evaluated for their performance by using each of the biocatalyst in 30-50 repeated conversion cycles for enzymatic amoxicillin synthesis.

The ability to catalyze the synthesis of amoxicillin using 6-APA and HPGMe as substrates in repeated conversion cycles using the same immobilized biocatalyst is expressed as % conversion of 6-APA. In a typical reaction, amount of enzyme used is equivalent to 15 U/ml-20 U/ml of reaction mixture containing 180 mM of 6-APA and 320 mM of HPGMe at 25° C., at pH 6.3. The reaction is determined by HPLC using Inertsil C8 column, mobile phase 1.2 ml/min flow rate with peak determined at 215 nm.

Each of the biocatalyst is used for 30-50 repeated conversion cycles for enzymatic amoxicillin synthesis with retention of activity up to 90% in reaction. Conversion of 6-APA is between 85-97-% for each batch cycle. Molar yield of Amoxicillin in each case is between 75-85%.

The biocatalysts prepared in the currents invention shows penicillin hydrolysis activity in the range of 800-2100 u/gm of dry weight and Cephalosporin G activity in the range of 1500-1800 u/gm dry weight and amoxicillin synthesis activity in the range of 110-350 units/gm dry weight.

The yields of the biocatalysts prepared according to the invention varies between 45-65% with respect to activity loaded in the process, in terms of hydrolytic activity with Penicillin G The non-limiting examples stated herein below elucidate the process in details highlighting the experimental variations of the process and various analytical parameters involved at each stage of process of product development and application of the product.

Example 1

Preparation of Enzyme Solution

Penicillin acylase enzyme was partially purified by precipitation with ammonium sulphate from solution of extracted proteins from r*E. coli* REIII (pKA18) at 5° C. and pH 7.5 and stirring for 30 minutes at 250 rpm followed by centrifugation at 4000 rpm at 5° C. obtain an enzyme precipitate. Ammonium sulphate equivalent to 20 gm per gm of proteins was used and protein was determined by Biuret reaction using BSA as standard. The resultant paste with dry weight in the range of 42-45% is diluted 1:1 with 0.1M sodium phosphate buffer pH 7.5.

Preparation of Polyvinyl Alcohol Solution (PVA) 10% w/w:
PVA (molecular weight 125000) was weighed in a preweighed glass container. Water was added to it and stirred in hot water bath to dissolve PVA till a clear solution was obtained.

Preparation of Gelatin Solution (10% w/w):
Gelatin (Bactogelatin, SD fine Ltd) was weighed in a preweighed glass container. Water was added to it and stirred in hot water bath to dissolve Gelatin till a clear solution is obtained.

Preparation of 0.1M Sodium Phosphate Buffer pH7.5:
4.5 gm of sodium dihydrogen orthophosphate and 10.4 gm of disodium hydrogen orthophosphate were weighed and 1000 ml of distilled water was added to dissolve. The pH of the resultant solution was 7.5.

4.0 gm of the above mentioned enzyme solution (hydrolytic activity of 1000 units/ml, 150 mg protein/ml) was allowed to stir in ice bath till a uniform suspension is obtained. 1.0 ml of 25% glutaraldehyde was added and stirred for 5 min (referred to as time of cross linking). To this, each of the above prepared solution of PVA and Gelatin prepared as above were added and allowed to mix for 2 mins. The reaction mixture was stirred till a coagulated gel aggregate was formed. This was refrigerated at 5° C. for at least 12-18 hours. The resultant gel aggregate was cut in pieces and sieved through #500 micron (#30 mesh) sieve. The gel aggregates were washed with water to remove traces of unreacted reagents and polymers. Further the aggregates, were stirred in 0.5% v/v solution of glutaraldehyde in 0.1M sodium phosphate buffer pH 7.5 at 25° C. for 30 minutes.

Final washing was done with water and immobilized product was stored in 50 mM sodium phosphate buffer containing 500 ppm of ethyl paraben.

The final product referred to as immobilized biocatalyst had dry weight in the range of 15-20% with 98% of particles having size between 100-300 microns.

The yield in terms of weight was between 1.4-1.5 times the weight of enzyme added. The yield of biocatalyst in terms of hydrolytic activity with Penicillin G was between 45-65% with respect to activity loaded in the process.

The penicillin hydrolysis activity was determined by alkalimetric titration using 25 mM Penicillin G, 50 mM sodium phosphate buffer pH 8.0

Example 1A 2000 gm of the enzyme paste as mentioned in example 1 was diluted with 12 l of 0.1M sodium phosphate buffer pH 7.5 (buffer prepared as in example 1). After dilution, Penicillin G hydrolytic activity was 464 Units per ml, the concentration of protein in the solution was 16.5 mg/ml. The enzyme suspension was stirred at 21° C. and pH of 7.5 was adjusted with 40% sodium hydroxide solution.

To this suspension, 527 grams per liter of solid ammonium sulphate was added slowly over 20 minutes by maintaining the pH to 7.5 by the addition of 40% sodium hydroxide solution.

To this 388 ml of glutaraldehyde (25% w/v solution) was added slowly in the course of 30 min maintaining the pH at 7.5 with 40% sodium hydroxide solution and temperature at 21° C. The resultant suspension was stirred for additional 1 hour (referred to as period of time of CLEA formation). The insoluble precipitate formed was washed six times with equivalent volume of 1M sodium chloride solution. The resultant cross linked aggregate was sieved through 200 micron sieve. The yield of hydrolytic activity (11000 U/gm dry weight) was 50% and yield in terms of weight was 91%

Example 1B 2000 gm of the enzyme paste as mentioned in example 1 was diluted with 12 l of 0.1M sodium phosphate buffer pH 7.5 (buffer prepared as in example 1). After dilution, Penicillin G hydrolytic activity was 464 Units per ml, the concentration of protein in the solution was 16.5 mg/ml. The enzyme suspension was stirred at 21° C. and pH of 7.5 was adjusted with 40% sodium hydroxide solution.

To this suspension, 527 grams per liter of solid ammonium sulphate was added slowly over 20 minutes by maintaining the pH to 7.5 by the addition of 40% sodium hydroxide solution.

To this 243 ml of glutaraldehyde (25% w/v solution) was added slowly in the course of 30 min maintaining the pH at 7.5 with 40% sodium hydroxide solution and temperature at 25° C. The resultant suspension was stirred for additional 1 hour (referred to as period of time of CLEA formation). The insoluble precipitate formed was washed six times with equivalent volume of 1M sodium chloride solution. The resultant cross linked aggregate was sieved through 200 micron sieve. The yield of hydrolytic activity (16000 U/gm dry weight) was 70% and yield in terms of weight was 87%.

Example 2

The process as in example 1 was repeated with enzyme precipitate obtained from rE. coli BL21 CCM7394 (synthetic activity for amoxicillin of 210 U/gm, protein 0.143 gm/gm). The final product referred to as immobilized biocatalyst had dry weight in the range of 17-21% with 98% of particles having size between 100-300 microns.

The yield of biocatalyst in terms of weight was between 1.5-2.0 times the weight of enzyme added. Amoxicillin Synthetic activity was determined using 44 mM 6-APA and 66 mM HPGMe, at pH 6.3 and 40° C. The reaction was carried out for 30 mins, followed by HPLC analysis. HPLC analysis was done with Inertsil C8 column, mobile phase 1.2 ml/min flow rate with peak determined at 215 nm The yield of biocatalyst in terms of synthetic activity for amoxicillin was between 40-45% with respect to activity loaded in the process.

Example 3

The process as in example 1 was repeated with enzyme precipitate obtained from rE. coli REXIII (pKX1P1) (synthetic activity for amoxicillin of 410 U/gm, protein 0.164 gm/gm). The final product referred to as immobilized biocatalyst had dry weight in the range of 17-23% with 98% of particles having size between 100-300 microns.

The yield of biocatalyst in terms of weight was between 1.5-1.8 times the weight of enzyme added. The yield of biocatalyst in terms of synthetic activity for amoxicillin was between 55-65% with respect to activity loaded in the process. Synthetic activity was determined by method described in Example 2.

Example 4

The immobilized biocatalyst was prepared as in example 1, but using varying concentration of Glutaraldehyde and time of cross linking. Table 1 summarizes the hydrolytic activity with respect to glutaraldehyde concentration and time of cross linking in the resultant immobilized biocatalyst.

TABLE 1

| Glutaraladhyde concentration | Time of cross linking Minutes | Yield of hydrolytic activity U/g dry weight |
| --- | --- | --- |
| 1.7 | 3 | 2055 |
| 1.7 | 10 | 1843 |
| 1.8 | 3 | 1752 |
| 1.8 | 10 | 1713 |
| 1.9 | 3 | 1690 |
| 1.9 | 10 | 1554 |
| 2.0 | 3 | 1480 |
| 2.0 | 10 | 1250 |

Example 5

The immobilized biocatalyst was prepared as in Example 2 but using varying concentration of Glutaraldehyde and time of cross linking. Table 2 below summarizes the synthetic activity with respect to glutaraldehyde concentration and time of cross linking in the resultant immobilized biocatalyst.

TABLE 2

| Glutaraladhyde concentration | Time of cross linking Minutes | Yield of synthetic activity U/g dry weight |
| --- | --- | --- |
| 1.0 | 3 | 180 |
| 1.0 | 10 | 164 |
| 1.3 | 3 | 151 |
| 1.3 | 10 | 145 |
| 1.5 | 3 | 118 |
| 1.5 | 10 | 101 |

Example 6

The immobilized biocatalysts were prepared as in Examples 1 and 2, but altering the ratio of both the entrapping agents, namely PVA and Gelatin to check the difference in the resultant product formed. The physical stability of each of the immobilized biocatalyst was critical parameter. The physical stability was determined by stirring a 5% w/v of suspended biocatalyst in water at 2000 rpm at room temperature for 20 mins and determining its filtration time through a 30µ filter. The filtrate was checked for the absorbance at 600 nm and 280 nm, which also indicates leaching of unbound gelatin and protein. Table 3 below summarizes the filtration time of each immobilized biocatalyst and its absorbance at 600 nm and 280 nm.

TABLE 3

| Sample no: | Immobilized catalyst | Ratio of PVA and Gelatin | Filtration time in sec | Absorbance 600 nm | Absorbance 280 nm | Activity Yield U/gd |
|---|---|---|---|---|---|---|
| 1 | Example 1 | 1:1.5 | 10 | 0.004 | 0.055 | 1748* |
| 2 | Example 2 | 1:1.5 | 10 | 0.006 | 0.088 | 214** |
| 3 | Example 1 | 1:1.3 | 15 | 0.056 | 0.104 | 1815* |
| 4 | Example 2 | 1:1.3 | 15 | 0.048 | 0.117 | 234** |
| 5 | Example 1 | 1:1 | 30 | 0.052 | 0.429 | 1583* |
| 6 | Example 2 | 1:1 | 30 | 0.037 | 0.376 | 176** |

* And ** means hydrolytic and synthetic activity, respectively.

FIGS. 1 and 2 indicate the stability and extent of protein leach.

Example 7

The immobilized biocatalyst was prepared as in example 1 wherein the materials used was a 15% solution of acrylamide, and N,N methylene bis acrylamide and gelatin. The solution contained each component in the ratio of 19:1:10 respectively. Buffered enzyme solution containing 100 mg of protein was allowed to form a uniform suspension with the above solution in an ice bath. Glutaraldehyde (25% solution) was added in 1.7% concentration based on protein equivalence and resultant mixture stirred for 2 mins. This was followed by addition of 1% (v/v) of ammonium persulphate and TEMED. The polymerization time was about 2 mins. The immobilized mass was refrigerated for 4 hrs, washed with distilled water, sieved in 500µ mesh and further stored in sodium phosphate buffer 50 mM.

The yield of biocatalyst in terms of weight was about 32% and hydrolytic activity yield was about 20%.

Example 8

Similar process as in Example 7 was followed but TEMED was replaced with 1% dimethylamino propionitrile to initiate polymerization.

The yield of biocatalyst in terms of weight was about 35% and hydrolytic activity yield was about 25%.

Example 9

The procedure as described in Example 7 was carried out using PVA in combination with acrylamide and N,N-methylene bis acrylamide instead of Gelatin, wherein the 15% solution was prepared in hot water for dissolution and cooled before addition to the enzyme solution.

The resultant immobilized catalyst was in form of irregular fibers instead of beads obtained in Example 7 and the yield in terms of hydrolytic activity was 27%.

Example 10

The procedure as described in Example 1 was carried out replacing PVA solution with 12% w/v chitosan and the concentration of gelatin used was 12% w/v.

Preparation of 12% w/v Solution of Chitosan:

12 gms of crab shell chitosan was dissolved in 40 ml of dilute acetic acid at 40° C. and neutralized to pH 7.0 with sodium acetate. The volume of the resultant solution was made to 100 ml with distilled water. The solution was cooled to room temperature before use. The immobilized catalyst prepared using chitosan had higher swell factor resulting in formation of soft gel with low mechanical stability as compared to the biocatalyst in Example 1.

Example 11

To the same enzyme solution as used in Example 1, was added 6 gm of solution of sodium alginate and polyvinyl alcohol mixed in the ratio of 1:1. The resulting suspension was stirred in ice for 5 minutes and added drop wise to prechilled 0.2M calcium chloride solution, containing 0.8 ml of 25% glutaraldehyde and stirred for 1 hr. The product was obtained in the form of clumps instead of beads with less mechanical strength. The product was washed with water. The yield in terms of weight was about 4% and hydrolytic activity determined was 240 U/gm dry weight.

Example 12

Determination of S/H ratio of the native and immobilized biocatalyst in Example 1, 2, 3, 4 is determined as follows. Each of the enzyme is allowed to react in solution of 0.1M ammonium phosphate buffer (pH 7.0) containing 50 mmoles of 6-APA and 100 mmoles of HPGMe at 15° C. for 30 mins. Samples are withdrawn at 0, 5, 10, 15, 20 minutes of the reaction to be analyzed by HPLC. The data obtained with different types of biocatalysts are evaluated in terms of amoxicillin synthesis (S) and hydrolysis of ester (H). Table 4 gives the S/H ratio of the immobilized and native enzymes.

TABLE 4

| Biocatalyst type | S/H ratio |
|---|---|
| Native Penicillin acylase used in Example 1 | 1.7 |
| Immobilized biocatalyst in Example 1 | 1.5 |
| Native enzyme used in Example 2 | 2.6 |
| Immobilized biocatalyst used in Example 2 | 2.4 |
| Native enzyme used in Example 3 | 3.1 |
| Immobilized biocatalyst used in Example 3 | 3.0 |

Example 13

The procedure as described in Example 1 was carried out using the enzyme preprocessed in the following manner:

Enzyme paste was suspended in 5 times of weight of buffer volume and stirred at 2° C. (as described in Example 1) followed by addition of 1.7% glutaraldehyde equivalent to the proteins in the solution. The mixture was stirred for 2 hrs maintaining the pH at 7.5 with ammonia and centrifuged to obtain an insoluble material with particles of size between 50 and 100 microns and processed further as in Example 1.

The final immobilized biocatalyst was obtained as fine granules, the size of which was between 50 and 150 micron, with more moisture retention.

Example 14

The biocatalyst prepared in Example 1 is used for preparation of 6-APA in repeated conversion cycles with the biocatalyst being recycled. The reaction time was about 65-70 minutes for 50 consecutive cycles. For each cycle, the enzyme:penicillin G potassium used was in ratio 1:1 (wet weight/w), at 28° C., with 8% substrate concentration and pH regulated at 8.0 with 2M ammonia. 6-APA formed was determined by HPLC. using Zorbax SB C18 column, mobile phase 0.05M KH2PO4 (pH 7.0):acetonitrile used in ratio 70:30, flow rate 1 ml/min and peak determined at 215 nm. The conversion of Penicillin G to 6-APA was 89% to 90% on molar basis with purity of 6-APA being in the range 98%-98.5%.

Example 15

The biocatalyst prepared in Example 1 is used for preparation of 6-APA similarly as in Example 14 using enzyme: penicillin G potassium in ratio 0.5:1 (w/w), at 28° C., with 8% substrate concentration and pH regulated at 8.0 with 2M ammonia. The reaction time was about 75-80 minutes for 20 consecutive cycles. The conversion of Penicillin G to 6-APA monitored by HPLC was 86% to 88% on molar basis with purity of 6-APA being 96%.

Example 16

The biocatalyst prepared in Example 7 is used for preparation of 6-APA in subsequent cycles with the biocatalyst being recycled. The reaction time was about 80-90 minutes for 5 consecutive cycles. For each cycle, the enzyme:penicillin G potassium used was in ratio 1:1 (wet weight/w), at 28° C., with 8% substrate concentration and pH regulated at 8.0 with 2M ammonia. The conversion of Penicillin G to 6-APA monitored by HPLC was 82.7% to 84% on molar basis with purity of 6-APA was 90.2%

Example 17

The biocatalyst prepared in Example 8 is used for preparation of 6-APA in subsequent cycles with the biocatalyst being recycled. The reaction time was about 85-90 minutes for 5 consecutive cycles. For each cycle, the enzyme:penicillin G potassium used was in ratio 1:1 (wet weight/w), at 28° C., with 8% substrate concentration and pH regulated at 8.0 with 2M ammonia. The conversion of Penicillin G to 6-APA monitored by HPLC was 82.7% to 86% on molar basis with purity of 6-APA being in the range 94-95%.

Example 18

The biocatalyst prepared in Example 9 is used for preparation of 6-APA in subsequent cycles with the biocatalyst being recycled. The reaction time was 55-60 minutes for 5 consecutive cycles. For each cycle, the enzyme:penicillin G potassium used was in ratio of 1:1 (wet weight/w), at 28° C., with 8% substrate concentration and pH regulated at 8.0 with 2M ammonia. The conversion of Penicillin G to 6-APA monitored by HPLC was 84% to 86% on molar basis with purity of 6-APA being in the range 90-92%.

Example 19

The biocatalyst prepared in Example 10 is used for preparation of 6-APA in subsequent cycles with the biocatalyst being recycled. The reaction time was about 65-70 minutes for 20 consecutive cycles. For each cycle, the enzyme:penicillin G potassium used was in ratio 1:1 (wet weight/w), at 28° C., with 8% substrate concentration and pH regulated at 8.0 with 2M ammonia. The conversion of Penicillin G to 6-APA monitored by HPLC was 84% to 87% on molar basis with purity of 6-APA being in the range 97% to 97.5%

Example 20

The biocatalyst prepared in Example 1 is used for preparation of 7-ADCA in 50 subsequent cycles with the biocatalyst being recycled. The reaction time was about 45-50 minutes for 75 repeated cycles. For each cycle, the enzyme: cephalosporin G used was in ratio 1:1.32 (w/w), at 28° C., with 4.5% substrate concentration and pH regulated at 8.0 with 2M ammonia. The conversion of cephalosporin G to 7-ADCA monitored by HPLC was between 86% to 87% on molar basis with purity of 7-ADCA being in the range 97-98%.

Example 21

The biocatalyst prepared in Example 2 was used for 30 repeated conversion cycles for enzymatic synthesis of Amoxicillin, wherein the 6-APA and HPGMe were used in the ratio of 180 mmoles:320 mmoles, at 25° C., pH maintained at 6.3 with 1:1 ammonia and enzyme was used in amount equivalent to 15 U/ml of amoxicillin synthetic activity.

The reaction time was based on % conversion of 6-APA: 88-93% conversion was reached in 90 minutes with less than 5% loss in activity and amoxicillin was obtained with purity of 96-99%. (Table 7 FIG. 5)

TABLE 7

| cycle no. | % Conv. (6-APA) | % Conv. (Amoxi) | Molar Yield | % purity HPLC |
|---|---|---|---|---|
| 1 | 97.63 | 111.09 | 80.21 | 98.3 |
| 2 | 90.77 | 97.28 | 80.13 | 97.5 |
| 3 | 83.05 | 91.18 | 78.91 | 99.2 |
| 4 | 85.27 | 87.82 | 80.09 | 97.35 |
| 5 | 88.4 | 110.5 | 81.43 | 99.3 |
| 6 | 92.19 | 107.79 | 80.84 | 99.1 |
| 7 | 89.14 | 102.5 | 80.79 | 98.07 |
| 8 | 89.49 | 98.6 | 80.88 | 98.97 |
| 9 | 89.2 | 84.81 | 83.62 | 99.11 |
| 10 | 93.08 | 111.48 | 83.94 | 98.53 |
| 11 | 94.64 | 108.3 | 84.41 | 98.65 |
| 12 | 94.18 | 100 | 78.88 | 99.12 |
| 13 | 93.02 | 87.53 | 79.6 | 97.99 |
| 14 | 92.82 | 89.84 | 78.48 | 97.99 |
| 15 | 86.9 | 85.93 | 79.35 | 98.27 |
| 16 | 88.04 | 100.49 | 83.25 | 99.2 |
| 17 | 90.9 | 88.39 | 79.3 | 97.84 |
| 18 | 84.24 | 86.39 | 80.42 | 98.75 |
| 19 | 88.78 | 105.75 | 80 | 97.86 |
| 20 | 91.37 | 95.78 | 82.26 | 99.15 |
| 21 | 87.29 | 87.39 | 81.05 | 98.32 |
| 22 | 93.92 | 83.07 | 78.41 | 98.36 |
| 23 | 90.81 | 103.13 | 78.34 | 96.99 |
| 24 | 89.75 | 114.93 | 84.45 | 97.46 |
| 25 | 94.81 | 84.66 | 80.05 | 98.12 |
| 26 | 90.98 | 82.74 | 80.05 | 99.85 |
| 27 | 81.99 | 85.99 | 79.53 | 98.05 |
| 28 | 87.99 | 99.04 | 79.68 | 99.23 |
| 29 | 91.22 | 107.05 | 79.94 | 98.08 |
| 30 | 86.56 | 98.3 | 75.98 | 97.75 |

Example 22

The biocatalyst prepared in Example 3 was used 50 repeated conversion cycles for enzymatic synthesis of Amoxicillin in 50 subsequent cycles, wherein the 6-APA and HPGMe were used in the ratio of 180 mmoles:320 mmoles, at 25° C., pH maintained at 6.3 with 1:1 ammonia and enzyme was used in amount equivalent to 15 U/ml of amoxicillin synthetic activity.

The reaction time was based on % conversion of 6-APA: 90-94% conversion was reached in 60 minutes with less than 5% loss in activity and amoxicillin was obtained with purity of 97-99%. (Table 8 FIG. 6)

TABLE 8

| cycle no. | % Conv. (6-APA) | % Conv. (Amoxi) | Molar Yield | % purity HPLC |
|---|---|---|---|---|
| 1 | 92.4 | 98.3 | 84.21 | 98.27 |
| 2 | 93.6 | 99.4 | 85.13 | 97.99 |
| 3 | 94.1 | 103.3 | 86.91 | 97.16 |
| 4 | 93.8 | 104.6 | 81.09 | 97.51 |
| 5 | 92.9 | 106.13 | 82.43 | 97.82 |
| 6 | 91.9 | 105.6 | 83.84 | 98.95 |
| 7 | 93.5 | 99.8 | 82.79 | 96.83 |
| 8 | 94.69 | 108.12 | 84.88 | 98.47 |
| 9 | 92.65 | 100.3 | 82.62 | 97.99 |
| 10 | 93.63 | 104.2 | 84.94 | 97.16 |
| 11 | 92.99 | 105.8 | 84.41 | 97.51 |
| 12 | 91.93 | 99.3 | 82.88 | 97.82 |
| 13 | 92.7 | 99.5 | 84.6 | 98.95 |
| 14 | 93.1 | 104.3 | 83.48 | 97.99 |
| 15 | 92.9 | 105.6 | 85.35 | 98.9 |
| 16 | 93.4 | 106.7 | 84.25 | 97.16 |
| 17 | 91.8 | 109.1 | 82.3 | 97.51 |
| 18 | 90.95 | 102.6 | 81.42 | 97.82 |
| 19 | 93.4 | 106.3 | 82.3 | 98.95 |
| 20 | 93.69 | 108.2 | 83.26 | 97.09 |
| 21 | 92.8 | 99.6 | 81.56 | 99.2 |
| 22 | 92.4 | 98.8 | 83.41 | 96.34 |
| 23 | 94 | 102.5 | 84.34 | 98.22 |
| 24 | 92.6 | 103.6 | 84.45 | 99.06 |
| 25 | 93.6 | 108.4 | 82.05 | 98.96 |
| 26 | 92.9 | 104.6 | 83.05 | 98.52 |
| 27 | 93.1 | 98.5 | 82.53 | 99.01 |
| 28 | 92.4 | 99.6 | 81.68 | 98.37 |
| 29 | 92.7 | 99.4 | 83.94 | 98.22 |
| 30 | 93.2 | 101.2 | 85.98 | 99 |
| 31 | 94.7 | 97.5 | 82.96 | 98.9 |
| 32 | 93.8 | 98.3 | 82.5 | 99.5 |
| 33 | 93.5 | 99.5 | 83.6 | 99.31 |
| 34 | 92.8 | 103.7 | 79.9 | 99.8 |
| 35 | 94.2 | 102.05 | 81.9 | 98.9 |
| 36 | 93.6 | 106.03 | 82.6 | 99.01 |
| 37 | 92.5 | 99.05 | 82 | 98.05 |
| 38 | 91.9 | 98.04 | 83.1 | 99.07 |
| 39 | 92.7 | 98.63 | 84.2 | 98.89 |
| 40 | 93.8 | 98.3 | 83.5 | 99.42 |
| 41 | 94.2 | 98.9 | 82.6 | 99.08 |
| 42 | 93.7 | 99.3 | 82.2 | 98.23 |
| 43 | 92.9 | 99.6 | 81.3 | 99.56 |
| 44 | 93.3 | 100 | 82.8 | 99.22 |
| 45 | 91.8 | 103.8 | 81.4 | 98.99 |
| 46 | 92.9 | 107.05 | 83.6 | 98.56 |
| 47 | 94.4 | 98.3 | 81.7 | 99.54 |
| 48 | 92.8 | 99.5 | 84.9 | 99.47 |
| 49 | 92.5 | 99.56 | 83.2 | 99.16 |
| 50 | 93.9 | 104.3 | 84.3 | 98.96 |

Example 23

The biocatalyst prepared in Example 3 was used for enzymatic synthesis of Amoxicillin, wherein the 6-APA and HPGMe were used in the ratio of 180 mmoles:255 mmoles, at 25° C., pH maintained at 6.3 with 1:1 ammonia and enzyme was used in amount equivalent to 15 U/ml of amoxicillin synthetic activity.

The reaction time was based on % conversion of 6-APA: 91% conversion was reached in 60 minutes and amoxicillin was obtained with purity of 98%.

Example 24

The biocatalyst prepared in Example 3 was used for enzymatic synthesis of Amoxicillin, wherein the 6-APA and HPGMe were used in the ratio of 180 mmoles:255 mmoles at 25° C., pH maintained at 6.3 with 1:1 ammonia and enzyme was used in amount equivalent to 10 U/ml of amoxicillin synthetic activity.

The reaction time was based on % conversion of 6-APA: 89.7% conversion was reached in 60 minutes and amoxicillin was obtained with purity of 97.82%.

Example 25

The biocatalyst prepared in Example 3 was used for synthesis of Amoxicillin, wherein the 6-APA and D-p-hydroxyphenylglycine N-propyl ester were used in the ratio of 180 mmoles:255 mmoles, at 25° C., pH maintained at 6.3 with 1:1 ammonia and enzyme was used in amount equivalent to 15 U/ml, of amoxicillin synthetic activity.

The reaction time was based on % conversion of 6-APA: 89.92% conversion was reached in 73 minutes and amoxicillin was obtained with purity of 97.16%.

Example 26

The biocatalyst prepared in Example 3 was used for synthesis of Amoxicillin, wherein the 6-APA and D-p-hydroxyphenylglycine isopropyl ester were used in the ratio of 180 mmoles:255 mmoles, at 25° C., pH maintained at 6.3 with 1:1 ammonia and enzyme was used in amount equivalent to 15 U/ml of amoxicillin synthetic activity.

The reaction time was based on % conversion of 6-APA: 93% conversion was reached in 75 minutes and amoxicillin was obtained with purity of 97.51%.

Example 27

The biocatalyst prepared in Example 3 was used for synthesis of Amoxicillin, wherein the 6-APA and D-p-hydroxyphenylglycine ethyl ester were used in the ratio of 180 mmoles:255 mmoles, at 25° C., pH maintained at 6.3 with 1:1 ammonia and enzyme was used in amount equivalent to 15 U/ml of amoxicillin synthetic activity.

The reaction time was based on % conversion of 6-APA: 88% conversion was reached in 71 minutes and amoxicillin was obtained with purity of 95%. (Table 9 FIG. 7)

TABLE 9

| Batch no. | Example 24 | Example 25 | Example 26 | Example 27 |
|---|---|---|---|---|
| Molar Yield % | 84.3 | 81.3 | 80 | 31.6 |
| % conv, 6-APA | 89.7 | 89.92 | 93 | 83 |
| Purity % | 97.82 | 97.16 | 97.51 | 97.82 |

Example 28

The effect of pH on the Penicillin G hydrolytic activity of biocatalyst prepared according to the Example 1 was determined in buffered solution at pH ranging from 6.5 to 9.0 at temperature 37° C. The profile of activity is shown in the FIG. 3 and table 5

TABLE 5

| pH | Activity U/gm wet |
|---|---|
| 6.5 | 253.5 |
| 7 | 267 |

TABLE 5-continued

| pH | Activity U/gm wet |
|---|---|
| 7.5 | 419.5 |
| 8 | 360.3 |
| 8.5 | 348.75 |
| 9 | 339.6 |

Example 29

The effect of reaction temperature on the hydrolysis of Penicillin G with biocatalyst prepared in Example 1 was determined in 50 mmoles of sodium phosphate buffer phosphate buffer, pH 8.0, at temperature ranging from 28° C. to 47° C. The profile is shown in the FIG. 4 and table 6

TABLE 6

| Temp | Activity U/gm wet |
|---|---|
| 28 | 301.4 |
| 35 | 354.2 |
| 37 | 360.3 |
| 42 | 386.2 |
| 47 | 417.11 |

CONCLUSION

The present invention explores in the area of improvement of immobilization methods of industrial enzyme using penicillin acylase and novel penicillin acylase as models. The novel catalysts prepared by optimized procedure described in this invention have multiple usage in hydrolytic and synthetic biocatalyses namely in the area of biotransformation of semi-synthetic beta-lactam antibiotics. In addition, the described process is simple to scale-up, involves the use of non toxic materials for immobilization. The process can be extended to use for other enzymes like lipase, invertase, protease etc.

REFERENCES

1. Biocatalyst in pharmaceutical and biotechnological industry: Edited by Ramesh N. Patel; CRC press-New York.
2. Immobilization of permeabilized whole cell penicillin G acylase from *Alcaligenes faecalis* using pore matrix crosslinked with glutaraldehyde by Cheng, Shiwei et al states Wei, Dongzhi[1]; Song, Qingxun; Zhao, Xiangguo, Biotechnology Letters, Volume 28, Number 14, July 2006, 1129-1133.
3. U.S. Pat. No. 4,727,030, Feb. 23, 1988, Fumihiro Ishimura, Koji Murata, Suong-Hyu Hyon, Yoshito Ikada
4. U.S. Pat. No. 4,978,619 titled "Enzyme immobilization by entrapment in a polymer gel matrix" by Kajiwara, Shigeru (Ibaraki, JP), Maeda, Hidekatsu (Nagareyama, JP), Suzuki, Hideo (Tokyo, JP)
5. Cross linked enzyme aggregates of Penicillin acylase: robust catalyst for the synthesis of beta lactam antibiotics, Adv synth, Catal, 343,559-576,2001 by Wegman, M. A., Janssen, M. H. A., van Rantwijk, F. et. al
6. Cross linked enzyme aggregates: a simple and effective method for the immobilization Penicillin acylase, Org Lett, 2, 1361-1364, 2000 by Coa, L., van Rantwijk, F, and Sheldon. R. A.
7. Wilson, L, Illanes, A., Pessela, B, et al, Enzcapsulation of cross linked penicillin G acylase aggregates in lentikats: evaluation of novel biocatalyst in organic media, Biotechnology Bioengineering, 86, 558-562, 2004
8. U.S. Pat. No. 5,846,762 titled "Structurally stable gel bead containing entrapped enzyme and method for manufacture thereof"
9. U.S. Pat. No. 6,060,268, 1998, De Vroom; Erik, Penicillin G acylase immobilized with a crosslinked mixture of gelled gelatin and amino polymer.
10. Structure and Applications of Polyvinyl alcohol Hydrogels produced by conventional cross linking or Freeing and thawing methods—Christie M. Hassan, Nikolaos A. Pepppas Advances in Polymer Sciences vol 153, 2000)
11. Gelatin manufactures institute of America-Gelatin information, news, history and more
12. U.S. Pat. No. 5,093,253 titled "Method for microbial immobilization by entrapment in gellan gum"

We claim:

1. A process for preparing a stable and viable biocatalyst; wherein said process comprises:
   (a) preparing Cross Linked Enzyme Aggregates from an enzyme by either:
      i) simultaneously precipitating the enzyme from a solution and cross-linking the enzyme with ammonium sulphate and glutaraldehyde at a temperature of between 0° C. and 2° C.; or
      ii) cross-linking the enzyme with ammonium sulphate and glutaraldehyde at a temperature of between 18° C. and 23° C. to obtain a self immobilized cross linked enzyme aggregate;
   (b) entrapping the Cross Linked Enzyme Aggregates in a solution of 10% w/w polyvinyl alcohol and 10% w/w gelatin at a temperature of 5° C.;
   (c) maintaining said solution of 10% w/w polyvinyl alcohol and 10% w/w gelatin at a temperature of 5° C. for 12 hours to obtain a gelled solution;
   (d) comminuting said gelled solution to produce gel aggregates having a particle size of between 100 and 300 microns; and
   (e) recrosslinking the gel aggregates with glutaraldehyde at 30° C. at a pH of between 7.5 and 7.6 to improve structural stability, thereby obtaining said biocatalyst as a product.

2. The process for preparing a stable and viable biocatalyst as claimed in claim 1, wherein the enzyme is Penicillin acylase obtained from rE. coli RE III bearing plasmid pKA18.

3. The process for preparing a stable and viable biocatalyst as claimed in claim 1, wherein the enzyme is novel Penicillin acylase obtained from *Achromobacter* sp. expressed in rE. coli BL21 CCM 7394 bearing plasmid pKX1P1.

4. The process for preparing a stable and viable biocatalyst as claimed in claim 1, wherein the enzyme is Penicillin acylase from *Achromobacter* sp. expressed in rE. coli RE III bearing the plasmid pKX1P1 (DVK strain).

5. The process for preparing a stable and viable biocatalyst as claimed in claim 1, wherein the concentration of ammonium sulphate used is between 10 and 50 gram per gram of protein.

6. The process for preparing a stable and viable biocatalyst as claimed in claim 1, wherein the concentration of glutaraldehyde used for crosslinking is between 1.7% v/v and 2.0% v/v and the concentration of glutaraldehyde used for recrosslinking is between 0.5% v/v and 0.7% v/v.

7. The process for preparing a stable and viable biocatalyst as claimed in claim 1, wherein the polyvinylalcohol concentration is between 4.5-7.5% of the weight of the biocatalyst obtained as the product.

8. The process for preparing a stable and viable biocatalyst as claimed in claim 1, wherein the said gelatin concentration is between 1-5% of the weight of the polyvinyl alcohol used.

9. The process for preparing stable and viable biocatalyst as claimed in claim 2, wherein the weight of the said biocatalyst is 1.4 to 1.5 times of the enzyme weight added.

10. The process for preparing stable and viable biocatalyst as claimed in claim 3, wherein the weight of the said biocatalyst is 1.5 to 2.0 times of the enzyme weight added.

11. The process for preparing stable and viable biocatalyst as claimed in claim 4, wherein the weight of the said biocatalyst is 1.5 to 1.8 times of the enzyme weight added.

12. The process for preparing stable and viable biocatalyst as claimed in claim 2, wherein the said biocatalyst shows penicillin hydrolysis activity in the range of 1800-2100 u/gm of dry weight and Cephalosporin G activity in the range of 1500-1800 u/gm dry weight.

13. The process for preparing stable and viable biocatalyst as claimed in claim 2, wherein the said biocatalyst yield is between 45-65% with respect to activity loaded in the process, in terms of hydrolytic activity with Penicillin G.

14. The process for preparing stable and viable biocatalyst as claimed in claim 3, wherein the said biocatalyst shows penicillin hydrolytic activity in the range of 800-900 units/gm dry weight and amoxicillin synthesis activity in the range of 110-200 units/gm dry weight.

15. The process for preparing stable and viable biocatalyst as claimed in claim 3, wherein the said biocatalyst yield is between 40-45% with respect to activity loaded in the process, in terms of hydrolytic activity with Penicillin G.

16. The process for preparing stable and viable biocatalyst as claimed in claim 4, wherein the said biocatalyst shows penicillin activity in the range of 1100-1500 U/gm dry weight and amoxicillin synthesis activity in the range of 250-350 u/gm dry weight.

17. The process for preparing stable and viable biocatalyst as claimed in claim 4, wherein the said biocatalyst yield is between 40-45% with respect to activity loaded in the process, in terms of hydrolytic activity with Penicillin G.

* * * * *